United States Patent
Lelic et al.

(10) Patent No.: US 8,839,746 B2
(45) Date of Patent: Sep. 23, 2014

(54) OXYGEN MEASURING APPARATUSES

(75) Inventors: Muhidin A. Lelic, Londonderry, NH (US); Thomas Corti, Hooksett, NH (US); Oduwa Osagiede, Derry, NH (US); Kenneth M. Swanson, Hollis, NH (US); John R. Devine, Londonderry, NH (US); Mike McCarron, Chelmsford, MA (US); Bryan Mills, Londonderry, NH (US)

(73) Assignee: UTC Fire & Security Corporation, Farmington, CT (US)

( * ) Notice: Subject to any disclaimer, the term of this patent is extended or adjusted under 35 U.S.C. 154(b) by 0 days.

(21) Appl. No.: 13/881,780

(22) PCT Filed: Oct. 29, 2010

(86) PCT No.: PCT/US2010/054733
§ 371 (c)(1),
(2), (4) Date: Apr. 26, 2013

(87) PCT Pub. No.: WO2012/057786
PCT Pub. Date: May 3, 2012

(65) Prior Publication Data
US 2013/0213279 A1 Aug. 22, 2013

(51) Int. Cl.
*F22B 7/18* (2006.01)
*F23N 5/00* (2006.01)
*F23N 1/02* (2006.01)
*F22B 35/00* (2006.01)
*G01N 33/22* (2006.01)

(52) U.S. Cl.
CPC ............... *F23N 1/022* (2013.01); *F23N 5/006* (2013.01); *F22B 35/00* (2013.01); *G01N 33/22* (2013.01); *Y02E 20/344* (2013.01)

USPC .................. 122/408.1; 122/135.1; 701/109; 204/424

(58) Field of Classification Search
CPC ............... F23N 2900/05005; F23G 2207/103
USPC ............... 122/135.1, 408.1, 448.1; 73/23.32, 73/114.73, 1.02; 701/109; 204/424
See application file for complete search history.

(56) References Cited

U.S. PATENT DOCUMENTS

| 4,152,232 A | * | 5/1979 | Otsuka et al. ............... 204/424 |
| 4,283,261 A | * | 8/1981 | Maurer et al. ............... 204/408 |

(Continued)

FOREIGN PATENT DOCUMENTS

WO    WO2007115855 A1    10/2007

OTHER PUBLICATIONS

PCT International Preliminary Report on Patentability and Written Opinion of the International Searching Authority for International Application No. PCT/US2010/054733, May 10, 2013, 5 pages.

*Primary Examiner* — Gregory A Wilson
(74) *Attorney, Agent, or Firm* — Cantor Colburn LLP

(57) ABSTRACT

An oxygen measuring apparatus (500) includes an inlet pipe (506) having a first end and a second end, an oxygen sensor (511) arranged inside the inlet pipe (506) between the first end of the inlet pipe and the second end of the inlet pipe, the oxygen sensor (511) having a communication medium (515) disposed thereon and extending through the second end of the inlet pipe (506), a filtering medium arranged (505) inside the inlet pipe between the oxygen sensor (511) and the first end of the inlet pipe, a housing (501) arranged against the second end of the inlet pipe, and a sensor control interface (512) arranged within the housing (501) and in communication with the communication medium (515) of the oxygen sensor (511).

20 Claims, 11 Drawing Sheets

(56) References Cited

U.S. PATENT DOCUMENTS

| | | | |
|---|---|---|---|
| 4,362,605 A * | 12/1982 | Bozon et al. | 205/784 |
| 5,917,135 A * | 6/1999 | Michaels et al. | 95/11 |
| 6,375,828 B2 * | 4/2002 | Ando et al. | 205/781 |
| 6,395,159 B2 * | 5/2002 | Matsuo et al. | 204/427 |
| 6,592,823 B1 | 7/2003 | Odermatt et al. | |
| 6,658,918 B2 * | 12/2003 | Hibino et al. | 73/31.05 |
| 6,660,143 B1 * | 12/2003 | Akatsuka et al. | 204/424 |
| 6,848,438 B2 * | 2/2005 | Celerier et al. | 123/672 |
| 7,370,545 B2 * | 5/2008 | Uchikawa et al. | 73/866.5 |
| 7,478,553 B2 * | 1/2009 | Higuchi | 73/114.73 |
| 8,602,772 B2 * | 12/2013 | Fan et al. | 431/2 |
| 2008/0190768 A1 * | 8/2008 | Kimata et al. | 204/429 |
| 2009/0182490 A1 * | 7/2009 | Saunders | 701/114 |
| 2009/0223466 A1 * | 9/2009 | Knorr, Jr. | 122/448.1 |
| 2009/0312938 A1 * | 12/2009 | Morita et al. | 701/109 |
| 2010/0174455 A1 * | 7/2010 | Powell | 701/51 |
| 2012/0034568 A1 * | 2/2012 | Pachner et al. | 431/12 |
| 2013/0042822 A1 * | 2/2013 | Fioriti et al. | 122/14.21 |

* cited by examiner

OXYGEN MEASURING APPARATUSES

FIELD OF INVENTION

The subject matter disclosed herein relates generally to the field of oxygen measurement, and more particularly to oxygen measurement in combustion control applications.

DESCRIPTION OF RELATED ART

In order to properly operate a boiler, it may be necessary to control a fuel/air ratio, boiler water level, and steam pressure/temperature of the boiler. Generally, there may be several actuators involved in control of these variables.

Conventionally, the fuel/air ratio is controlled throughout the entire operating range of the boiler to ensure boiler safety and combustion efficiency. Fuel/air ratio control is implemented through a coordinated mapping between fuel valve position and air damper position within a firing range of the boiler. If the coordinated relationship between the actuators is fixed through a mechanical system, then the combustion system is called a linkage combustion system. If the actuator positions are flexible and independently adjustable in response to process conditions (e.g. steam pressure/flow, or water temperature) then the combustion system may be a parallel positioning system (if without flow sensors for fuel/air ratio control) or a fully-metered system with installed fuel and air flow sensors for fuel/air ratio control.

BRIEF SUMMARY

According to one aspect of the invention, an oxygen measuring apparatus includes an inlet pipe having a first end and a second end, an oxygen sensor arranged inside the inlet pipe between the first end of the inlet pipe and the second end of the inlet pipe, the oxygen sensor having a communication medium disposed thereon and extending through the second end of the inlet pipe, a filtering medium arranged inside the inlet pipe between the oxygen sensor and the first end of the inlet pipe, a housing arranged against the second end of the inlet pipe, and a sensor control interface arranged within the housing and in communication with the communication medium of the oxygen sensor.

According to another aspect of the invention, an oxygen measuring apparatus includes an inlet pipe having a first end and a second end, an oxygen sensing cartridge arranged inside the inlet pipe, the oxygen sensing cartridge having an outer wall in contact with an inner wall of the inlet pipe, a first end in contact with the second end of the inlet pipe, a communication medium disposed thereon, and a filtering medium arranged therein, a housing arranged between the second end of the inlet pipe and the first end of the oxygen sensing cartridge, and a sensor control interface arranged within the housing and in communication with the communication medium of the oxygen sensing cartridge.

According to another aspect of the invention, a boiler control system includes a combustion chamber, a flue stack in communication with the combustion chamber, a closed-loop boiler control portion in communication with the flue stack and the combustion chamber, and an oxygen measuring apparatus arranged on the flue stack. The oxygen measuring apparatus includes an inlet pipe having a first end and a second end, the inlet pipe extending through a wall of the flue stack, an oxygen sensing cartridge arranged inside the inlet pipe, the oxygen sensing cartridge having an outer wall in contact with an inner wall of the inlet pipe, a first end in contact with the second end of the inlet pipe and the wall of the flue stack, a communication medium disposed thereon, and a filtering medium arranged therein, a housing arranged around the second end of the inlet pipe, the first end of the oxygen sensing cartridge, and against the wall of the flue stack, and a sensor control interface arranged within the housing and in communication with the communication medium of the oxygen sensing cartridge.

Other aspects, features, and techniques of the invention will become more apparent from the following description taken in conjunction with the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Embodiments of an oxygen measuring apparatus and control system are provided herein, with example embodiments being discussed below in detail.

As described herein, example embodiments provide a modular, low cost oxygen measuring apparatus that is relatively easy to maintain; relatively easy to calibrate, includes capability of monitoring/data acquisition, and has both digital and analog means of communications with subsystems and control systems.

Example embodiments may include a wideband Universal Exhaust Gas Oxygen (UEGO) Sensor/probe for use in monitoring oxygen concentration in combustion gas mixtures. The UEGO probe may be any suitable probe. For example, suitable probes may include oxygen monitoring probes typically used in automotive applications for emissions control. The UEGO probe control electronics may be responsible for exciting the oxygen sensor's heater to a suitable working temperature; responsible for monitoring the operating conditions of the oxygen sensor; and acquiring the sensor's O2 level signal for processing. The processed signal is subsequently provided to a control system as part of a feedback signal for a closed loop system, and/or provided to other suitable components for monitoring.

Example embodiments are capable of monitoring stack temperature of a boiler via a thermocouple or other suitable temperature measuring apparatus. Acquired temperature data may be used to derive combustion efficiency data, and/or for other purposes. Communication with the UEGO probe may be facilitated over a communications medium (e.g., Serial, CAN bus, modbus, etc) or as an analog voltage/current signal.

Hereinafter, example embodiments are described in detail.

Figure 1:
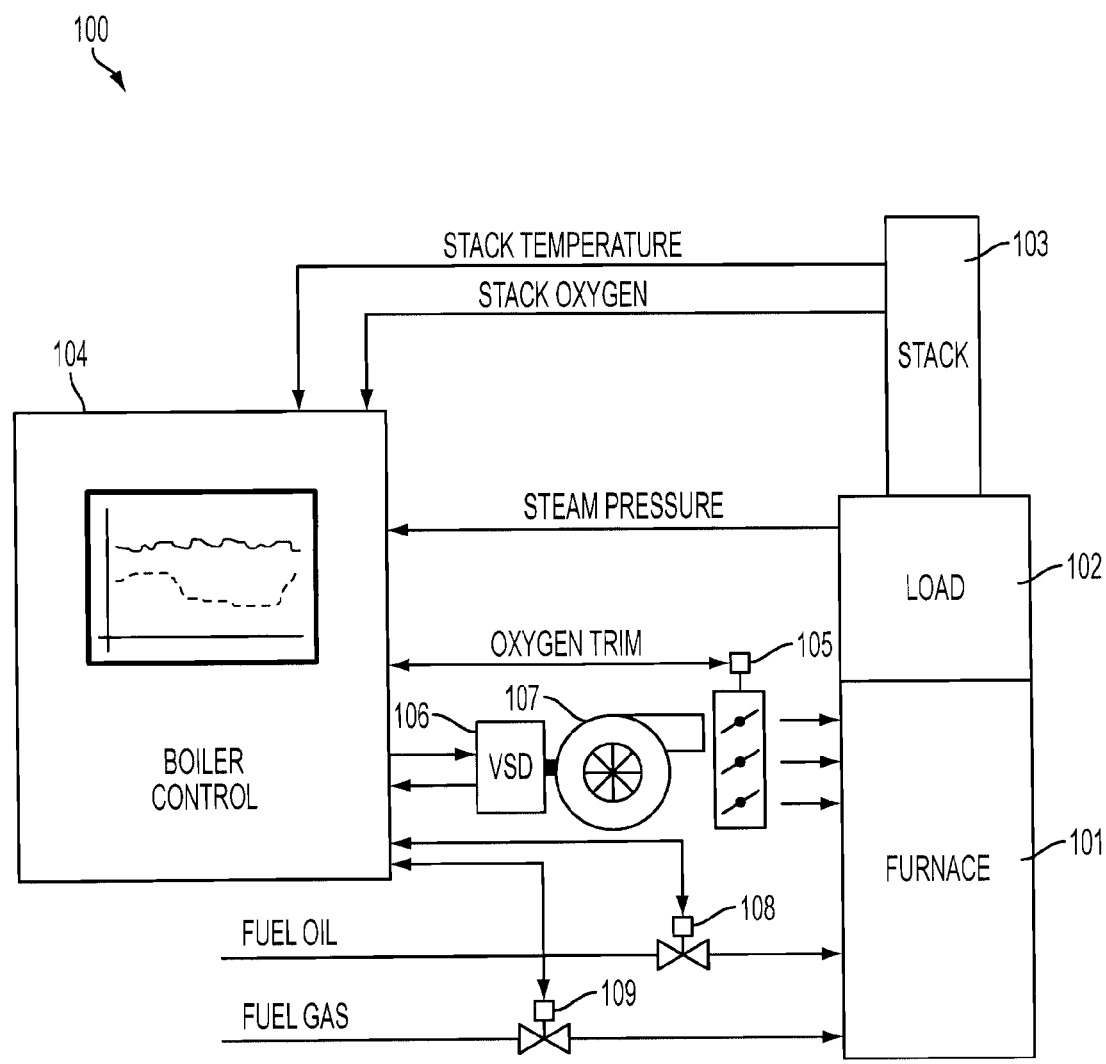
FIG. 1 depicts a boiler system with fuel and air flow control.

FIG. 1 depicts a boiler system. As illustrated, the system 100 includes a furnace/combustion chamber 101, a load 102 arranged on the boiler, and a stack 103 arranged on the load. The system 100 further includes a boiler control portion 104 in communication with the stack 103, the load 102, and the furnace/combustion chamber 101.

Stack temperature and oxygen information (e.g., from an oxygen measuring apparatus) may be provided to the boiler control portion 104 over a communication medium (e.g., Serial, CAN bus, etc), as a voltage/current signal, or as any suitable signal/data. Steam pressure information may be provided to the boiler control portion 104 over any suitable medium as described above. In response to the temperature, oxygen, and steam pressure information, the boiler control portion 104 may control fuel and air to maintain stable and/or efficient operation of the boiler system 100.

For example, the system 100 includes air driving fan 107 in communication with variable speed drive 106, which is in further communication with the boiler control portion 104. The system 100 further includes oxygen trim servo 105 in communication with the boiler control portion 104. The oxygen trim servo 105 may be arranged between the air driving fan 107 and the furnace/combustion chamber 101 such that air driven by the fan 107 may be forced through the servo 105 into the furnace/combustion chamber 101. Thus, the boiler control portion 104 may accurately control a level of oxygen and air entering the furnace/combustion chamber 101.

The system 100 further includes fuel oil control servo 108 and fuel gas control servos 109 in communication with the boiler control portion 104. The control servos 108-109 control the flow of fuel oil and fuel gas, respectively, entering the furnace/combustion chamber 101. Thus, the boiler control portion 104 may accurately control the flow of fuel oil or fuel gas entering the furnace/combustion chamber 101.

According to example embodiments, boiler control portions of boiler systems may include closed-loop boiler control models to accurately maintain operation of boiler systems and their efficiency.

Figure 2:
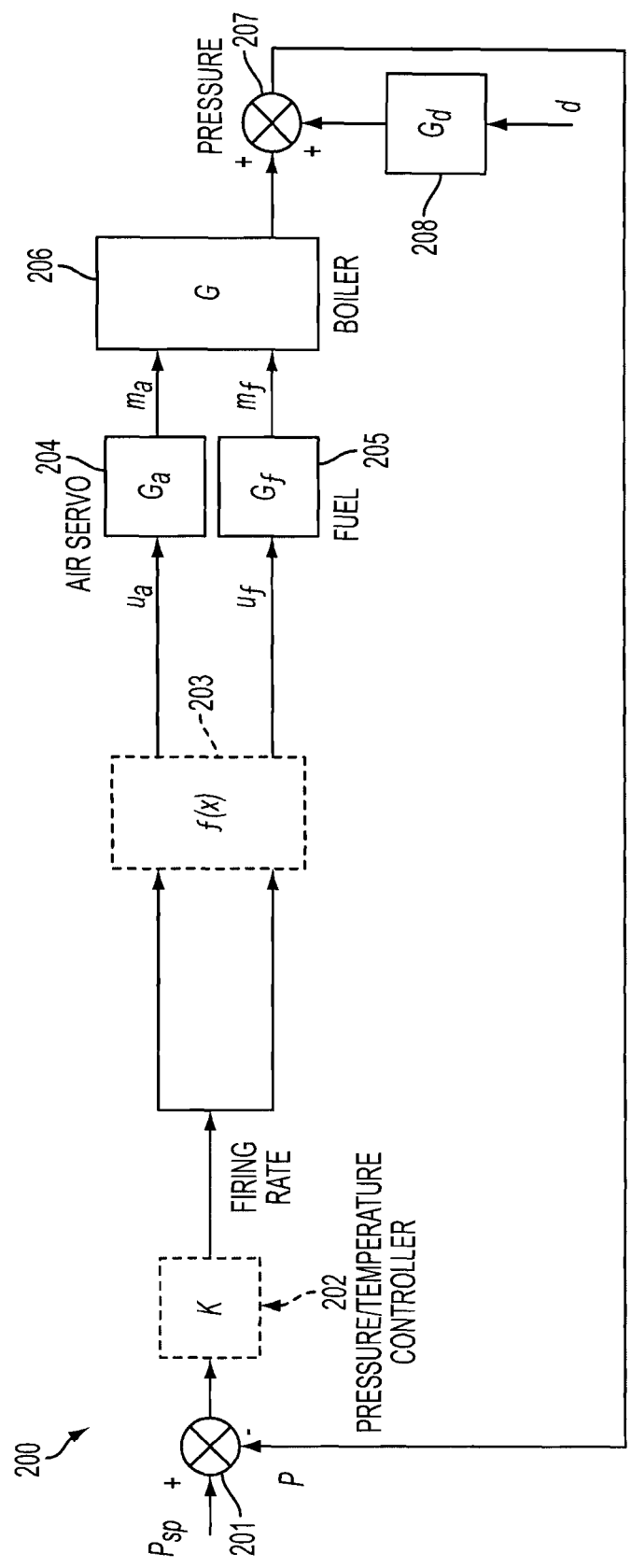
FIG. 2 depicts a parallel positioning closed-loop boiler control method, according to an example embodiment.

FIG. 2 depicts a parallel positioning closed-loop boiler control method, according to an example embodiment. As illustrated, the method 200 includes receiving a pressure value $P_{sp}$ of a boiler, and mixing the measured value with a calculated value at block 201. The mixed value is used to determine a firing rate through function K at block 202. Thereafter, a fuel/air servo mapping function f(x) is applied to the firing rate at block 203. The fuel/air servo map function 203 is determined over a boiler firing rate range during a commissioning process.

Outputs of the function f(x) are applied to transfer functions $G_a$ and $G_f$ at blocks 204 and 205, respectively. Subsequently, outputs of the transfer functions $G_a$ and $G_f$ are applied to boiler transfer function G at block 206. Outputs of the boiler transfer function G and an external disturbance transfer function $G_d$ (208) are mixed at 207 to determine the calculated value described with reference to block 201. Thus, boiler control method 200 is a closed loop control method.

Figure 3:
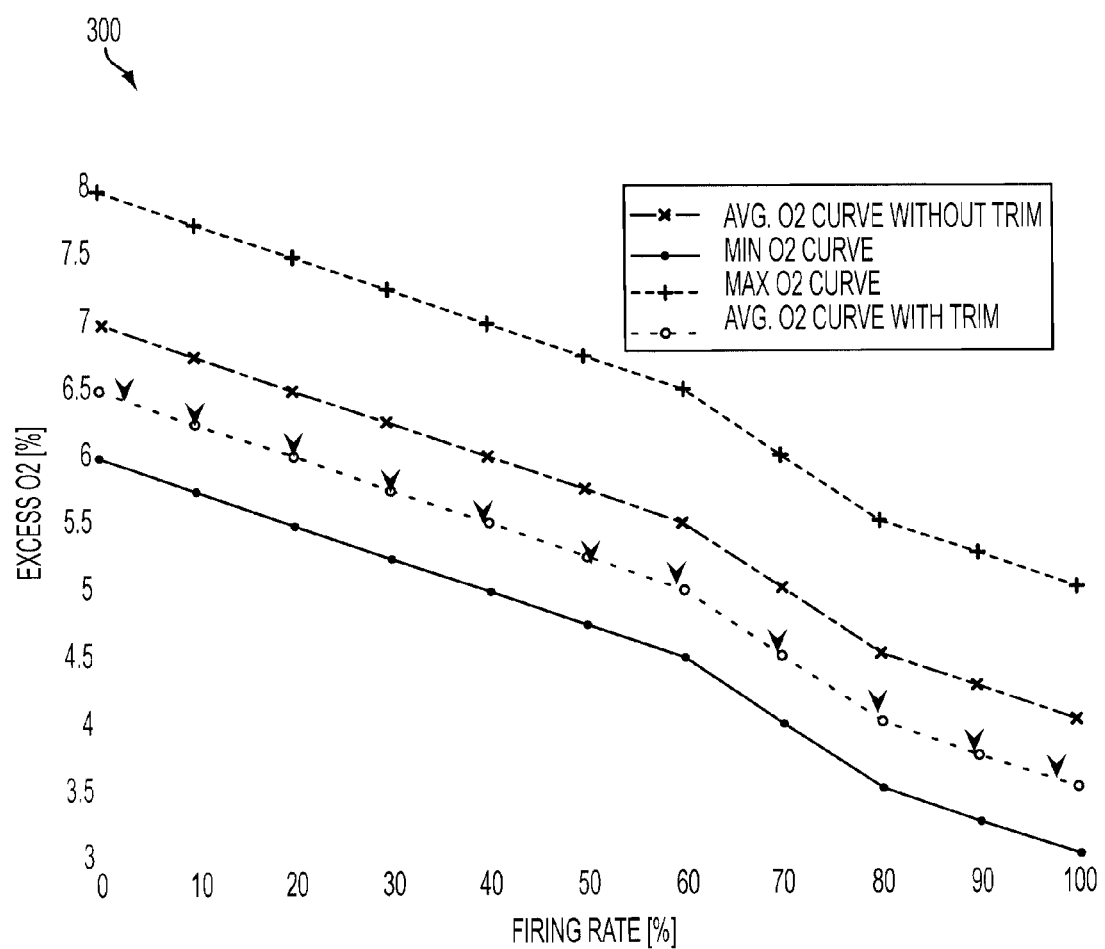
FIG. 3 depicts a graph of oxygen levels in a boiler.

Because the control system 200 does not include mass flow sensors for measuring air flow and fuel flow, flow through air and fuel servos may not be accurately controlled. Any changes in air or fuel, such as air density, temperature, humidity, or fuel supplied pressure, result in mass flow changes in air side or fuel side and fuel/air ratio will deviate from the fuel/air servo map generated at mapping function f(x) (203). This will cause variations in excess air levels. In order to prevent the excess air level from going too low which may cause unsafe boiler operation, the fuel/air servo map function should be defined such that there is enough excess air during the combustion process. However, too much excess air will result in lower combustion efficiency. FIG. 3 depicts excess oxygen curves compared to firing rates in graph 300. Generally, it may be necessary to have increased excess oxygen in lower firing rates compared with higher firing rates. This is mainly due to flame instability issues in the lower firing range. If there is no oxygen trim control, the oxygen curve could be between the maximum oxygen curve and the minimum oxygen curve of FIG. 3.

In order to obtain better combustion efficiency over a relatively long period of time, mass flow variations may be better addressed using oxygen trim control. This may be facilitated through control of the excess air/oxygen in a more precise manner. For example, in order to close the loop for oxygen trim, an oxygen sensor is needed to measure the excess air in the stack.

Figure 4:
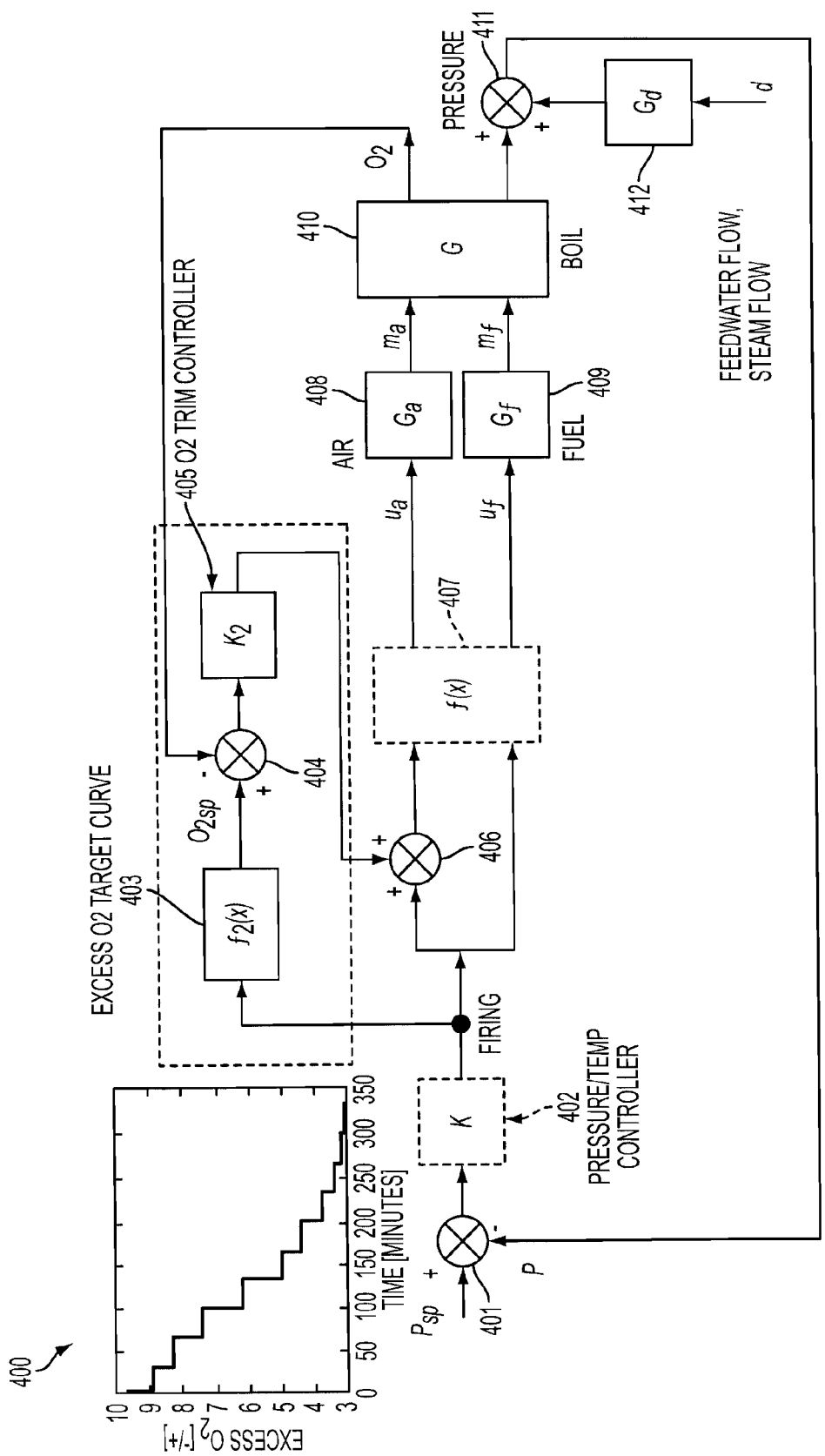
FIG. 4 depicts parallel positioning closed-loop boiler control method with oxygen trim, according to an example embodiment.

FIG. 4 depicts parallel positioning closed-loop boiler control method with oxygen trim, according to an example embodiment. As illustrated, the method 400 includes receiving a pressure value $P_{sp}$ of a boiler, and mixing the measured value with a calculated value at block 401. The mixed value is used to determine a firing rate through function K at block 402. Thereafter, a fuel/air servo mapping function f(x) is applied to the firing rate and a mixed oxygen trim level (406) at block 407.

Outputs of the function f(x) are applied to transfer functions $G_a$ and $G_f$ at blocks 408 and 409, respectively. Subsequently, outputs of the transfer functions $G_a$ and $G_f$ are applied to boiler transfer function G at block 410. Outputs of the boiler transfer function G and an external disturbance transfer function $G_d$ (412) are mixed at 411 to determine the calculated value described with reference to block 401.

Regarding the oxygen trim level, the firing rate calculated through function K is applied to a target excess oxygen curve at block 403. Subsequently, the applied curve is mixed with an oxygen output value from the boiler transfer function G at block 404. The mixed value is applied to oxygen trim transfer function K2 at block 405, and mixed with the firing rate at block 406, as described above. Thus, boiler control method 400 is a closed loop control method.

As described above, in order to trim oxygen in a boiler system more effectively, an oxygen measuring sensor or apparatus is necessary.

Figure 5:
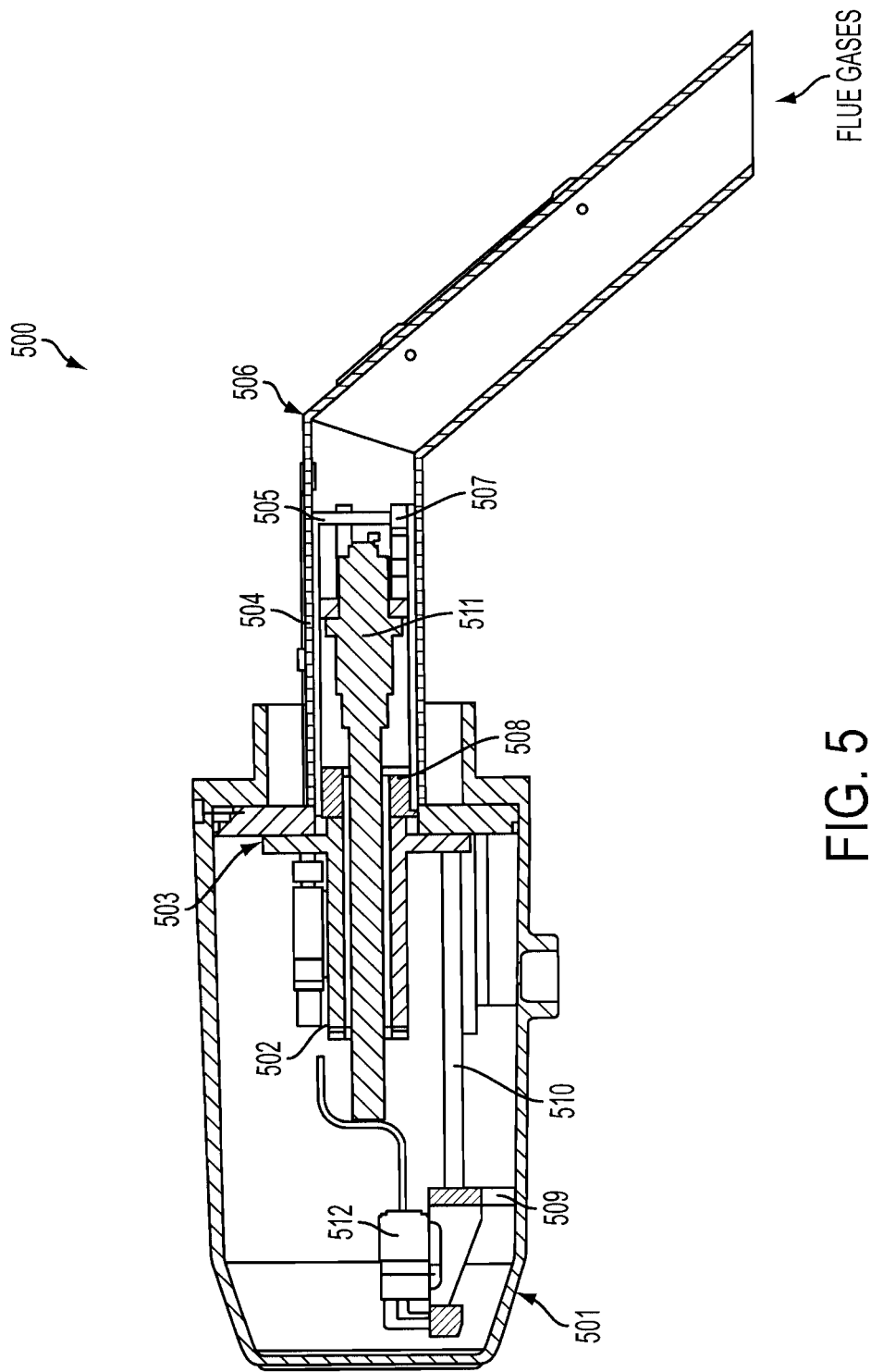
FIG. 5 depicts an oxygen measuring apparatus, according to an example embodiment.

FIG. 5 depicts an oxygen measuring apparatus, according to an example embodiment. As illustrated, the apparatus 500 includes housing 501. The housing 501 may be any suitable housing, including high-temperature resistant plastic, metal (e.g., aluminum), or any suitable material. The apparatus 500 further includes tubing 502 arranged within the housing 501. The tubing 502 may be any suitable tubing, including metal or aluminum tubing. The apparatus 500 further includes thermal gasket 503 disposed to seal tubing 502 within the housing 501 and against tubing 504. Tubing 504 may be any suitable tubing, for example, stainless steel, aluminum, or metal tubing. As illustrated, the tubing 504 may extend beyond the housing 501 and may curve or bend against tubing/pipe 506 to facilitate measurement of gases within a flue stack. For example, pipe 506 may extend into a flue stack and allow flue gases to enter one end, flow through filter 505, and be measured for oxygen content at sensor 511.

The filter 505 is arranged within the tubing 504, and disposed to filter gases entering the housing 501. The filter 505 may be any suitable filter, including mesh or micron filters. The filter 505 may be supported within the tubing 504 with screws, bolts, or any other suitable attachment means 507. The apparatus 500 further includes thermal break 508 disposed between an oxygen sensor 511 within the tubing 504 and the tubing 502. The thermal break 508 may be formed of any suitable material, including machinable ceramic, glass, or other suitable material.

The apparatus 500 further includes supporting rod(s) 510 disposed to support the thermal break 509 and the tubing 502 against an interior wall of the housing 501. A thermocouple and/or oxygen communication interface 512 is further included within the housing 501, which is in communication with a thermocouple and/or the oxygen sensor 511.

Figure 6:
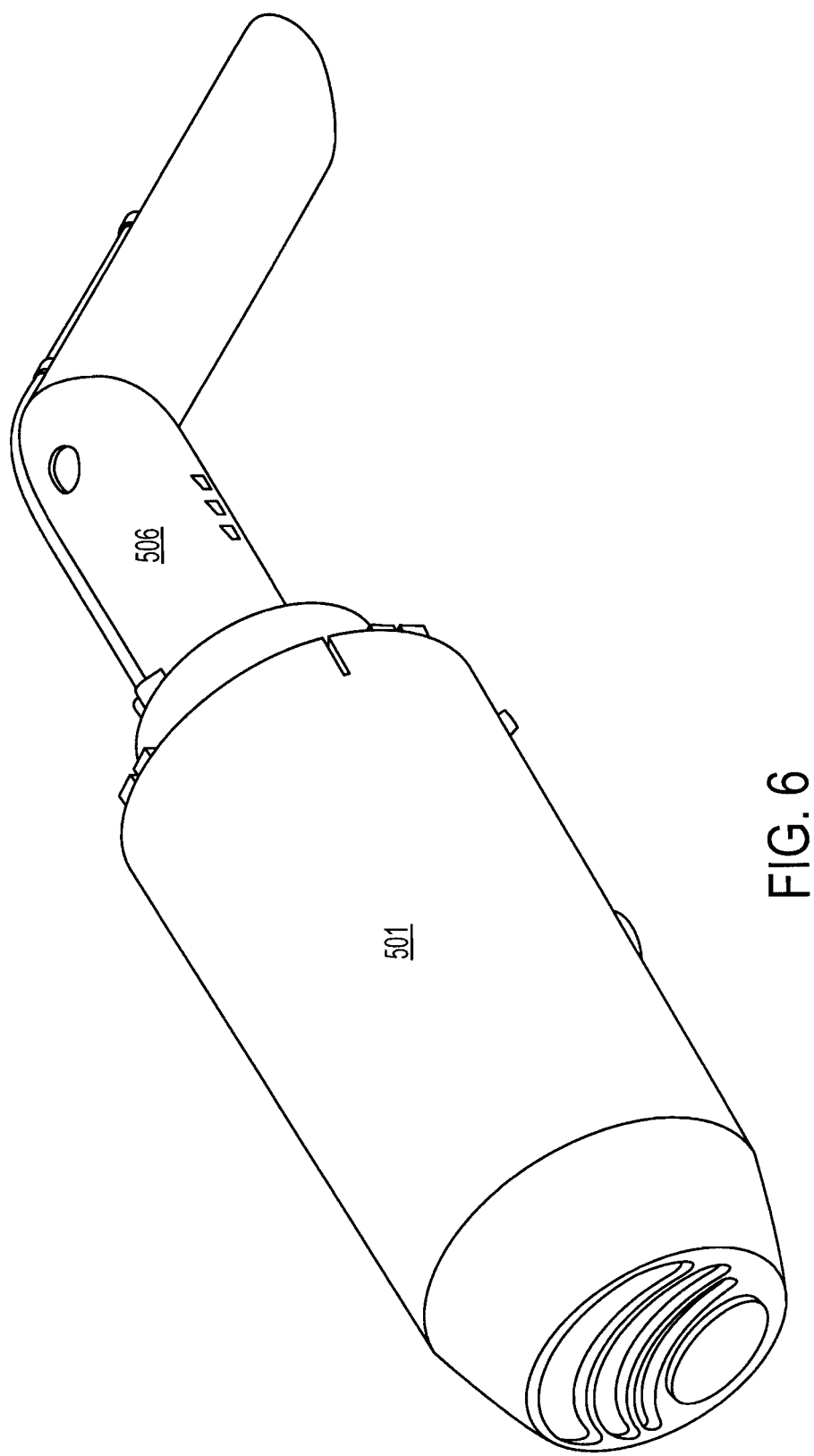
FIG. 6 depicts an oxygen measuring apparatus, according to an example embodiment.
Figure 7:
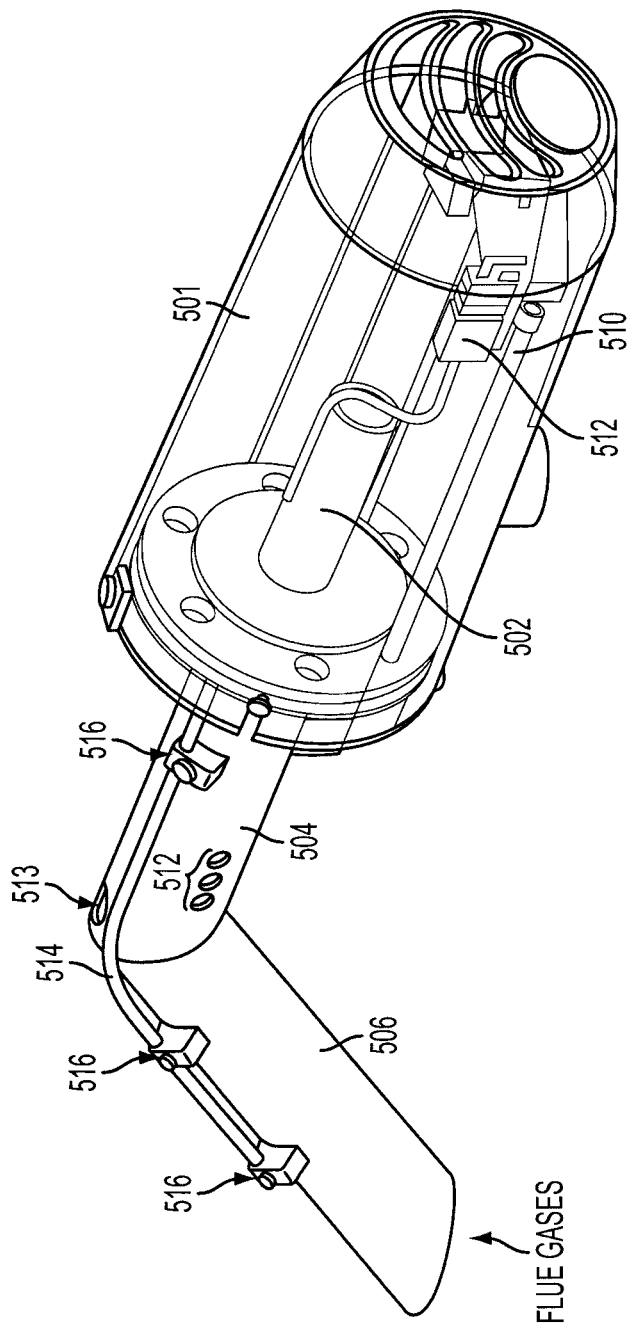
FIG. 7 depicts an oxygen measuring apparatus, according to an example embodiment.

FIG. 6 depicts a perspective view of the oxygen measuring apparatus 500 and FIG. 7 depicts an alternate perspective view of the oxygen measuring apparatus 500. The housing 501 is depicted as translucent in FIG. 7 for illustrative purposes, although a translucent/transparent high-temperature resistant plastic may be used for the housing 501. As illustrated in FIG. 7, thermo couple 514 is arranged on tubing/pipe 504/506 using supportive means 516. The supportive means 516 may be support portions welded, glued, or otherwise affixed to the tubing/pipe 504/506. Also, although described as a thermocouple, it should be understood that any suitable temperature measuring probe/apparatus may be used. As further illustrated, flue gas outlets 512-513 are arranged on the tubing/pipe 504/506. The flue gas outlets 512-513 may penetrate walls of the tubing/pipe 504/506 and be disposed to release a portion of flue gases entering the pipe 506 from a flue stack. In this manner, a relatively continuous sample of flue gases may flow through the filter 505 and be exposed against a sampling portion of the sensor 511. In order to further illustrate example embodiments, a detailed view of an oxygen probe portion/cartridge of the apparatus 500 is provided in FIG. 8.

Figure 8:
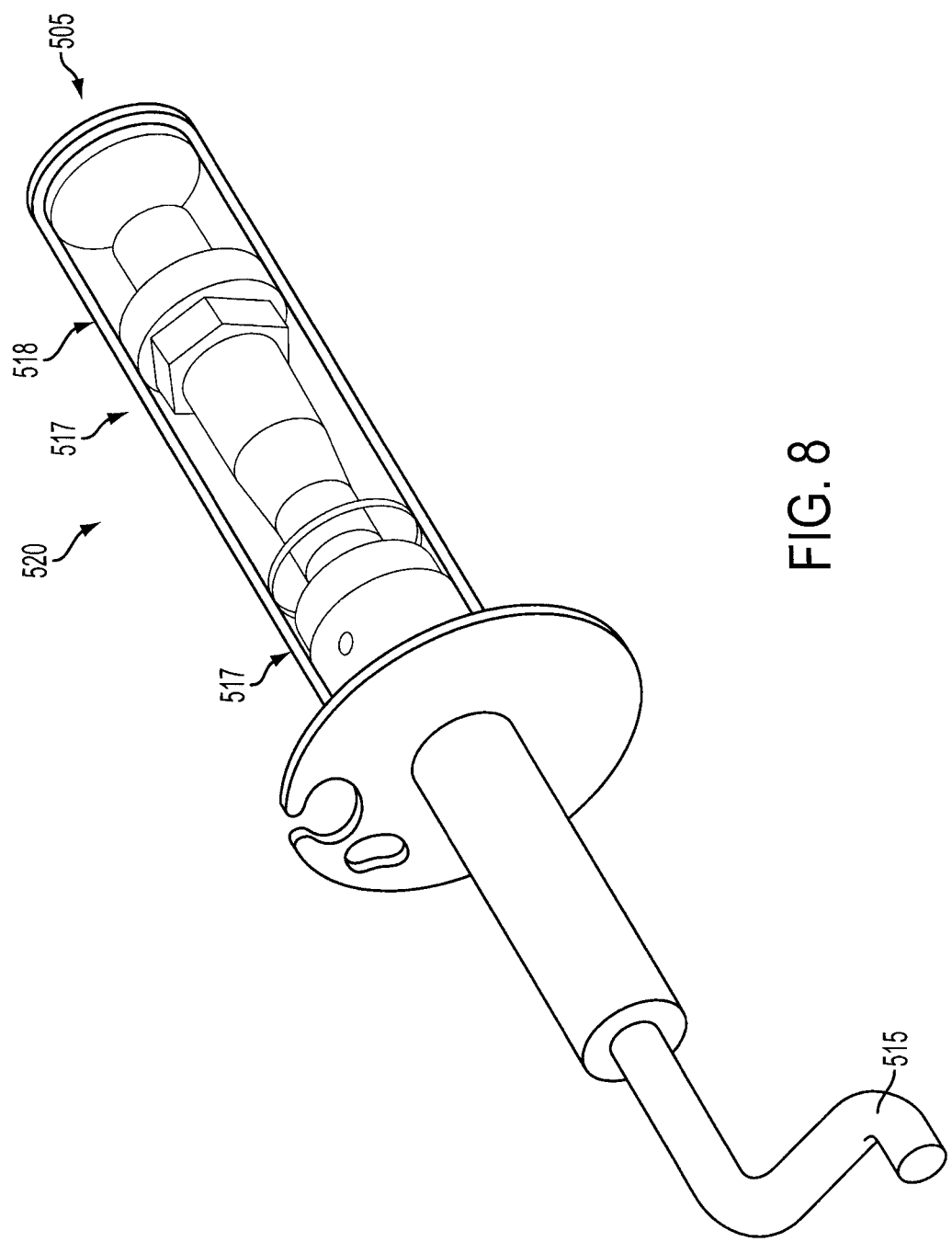
FIG. 8 depicts an oxygen probe portion of an oxygen measuring apparatus, according to an example embodiment.

FIG. 8 depicts an oxygen probe portion 520 of an oxygen measuring apparatus, according to an example embodiment. As illustrated, the probe 511 may be arranged within the portion 520 using attachment/supportive means 517. The means 517 may be nuts, bolts, spacers, or other supportive means. Furthermore, a gasket or sealing ring 518 may further support the probe 511 within the portion 520. The portion 520 may be entirely or partially arranged within the tubing 506 of the apparatus 500. Further, a communication medium 515 may extend from the oxygen probe 511 to an interior of the housing 501. The communication medium 515 may be connectable to the probe 511 and the communication portion/interface 512 described above. Alternatively, the communication medium 515 may be permanently affixed to the probe 511 (e.g., welded or soldered wire). The entire oxygen measuring portion 520 may be arranged as a replaceable cartridge to facilitate easy maintenance and calibration of the apparatus 500. Furthermore, as illustrated, the portion 520 may include an outer wall disposed to be in contact with an inner wall of the pipe 506.

Figure 9:
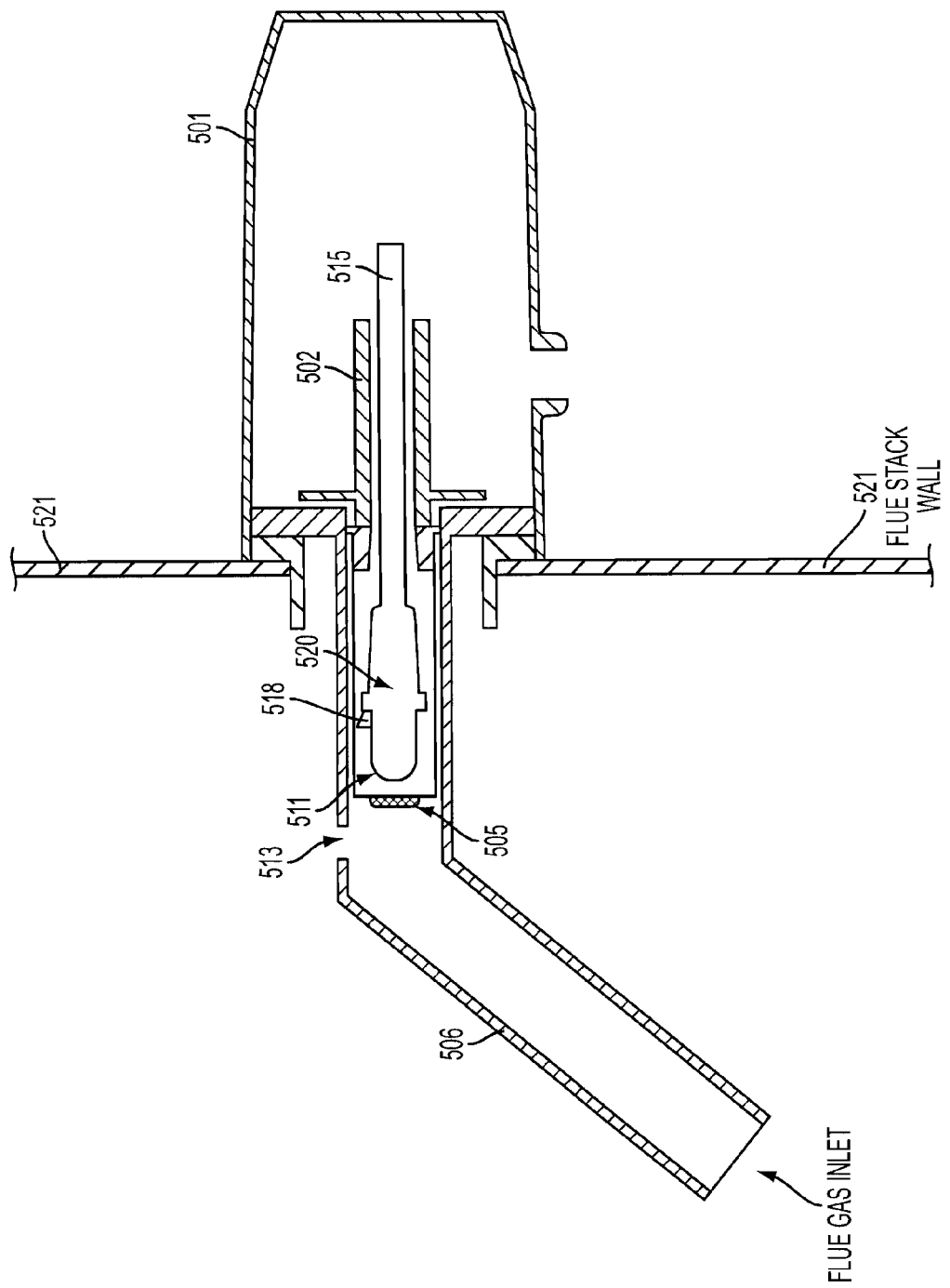
FIG. 9 depicts an oxygen measuring apparatus, according to an example embodiment.

FIG. 9 depicts the oxygen measuring apparatus 500 arranged on a flue stack wall 521. As shown, the housing 501 may be arranged against the wall 521 while the tubing/pipe 504/506 extends into the flue stack. In this manner, the housing 501 may protect the communications interface 512, while the oxygen measuring portion 520 may remain within the flue stack, thereby facilitating measurement of oxygen within the flue gases.

Figure 10:
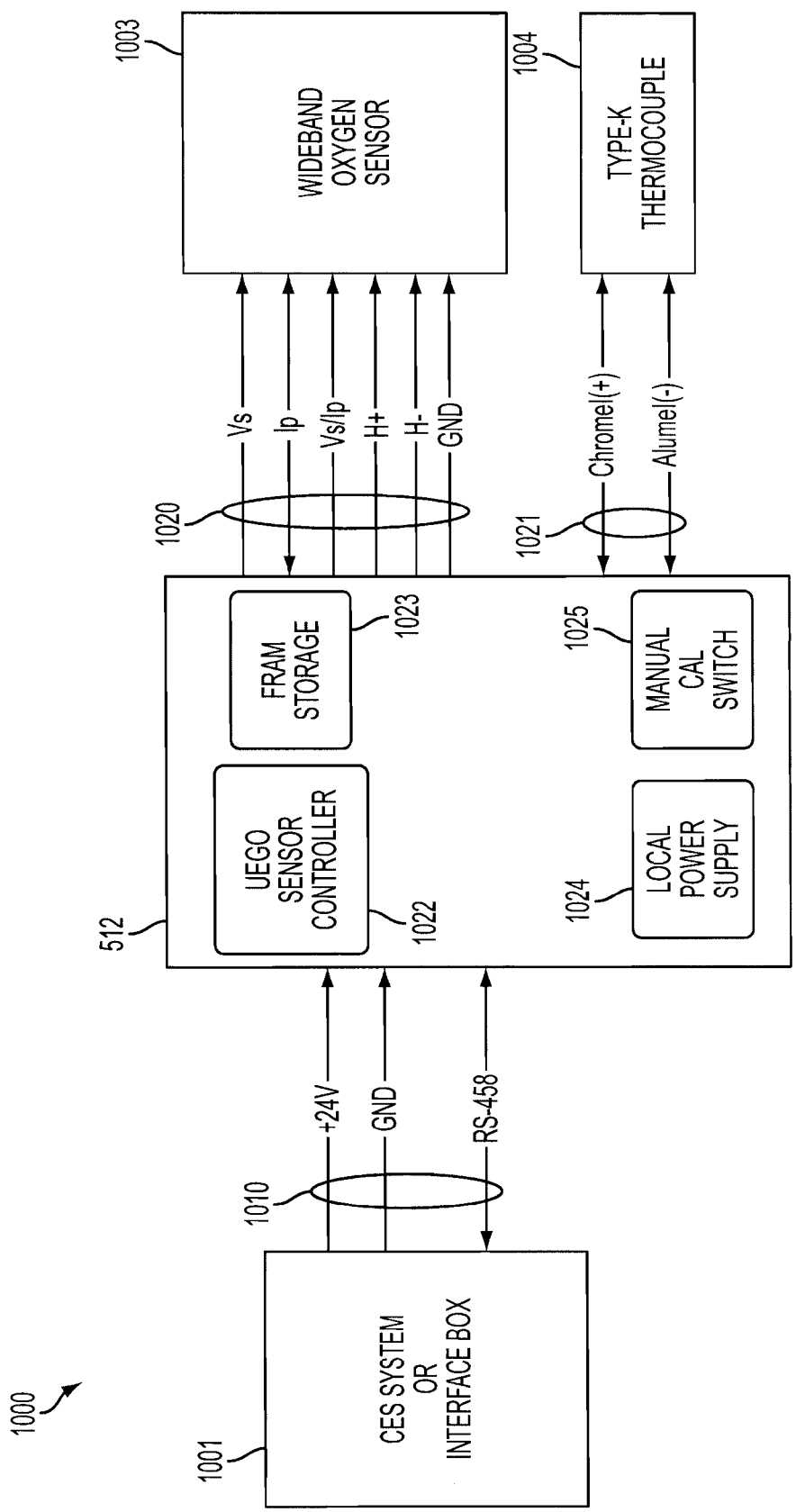
FIG. 10 depicts a control system of an oxygen measuring apparatus, according to an example embodiment.

FIG. 10 depicts a control system of an oxygen measuring apparatus, according to an example embodiment. The system 1000 includes the communications interface 512 in communication with an oxygen sensor 1003. The oxygen sensor 1003 may be somewhat similar to the oxygen sensor 511 described above. The interface 512 may include a sensor control portion 1022, storage portion 1023, a power supply 1024, and a calibration portion 1025. The sensor control portion 1022 may be a control portion disposed to provide control for sensor temperature, filter and condition signals from the sensor, and monitor health of the sensor. For example, in order to operate correctly, the sensor 1003 may need to be at a correct operating temperature. Furthermore, communication with the probe to retrieve oxygen information and monitor health is necessary. Thus, the sensor control portion 1022 may determine necessary parameters and provide/receive necessary signals over medium 1020. For example, medium 1020 may be somewhat similar to medium 515 described above. The interface 512 may be in further communication with thermocouple 1004 over medium 1021. For example, medium 1021 may be comprised of distinct metals which are welded at the thermo couple 1004 to retrieve a voltage indicative of temperature at the weld. Alternatively, medium 1021 may be a medium disposed to communication with any other temperature sensor, for example, a high-temperature resistant sensor capable of monitoring temperatures within a flue stack. Thus, the interface 512 may monitor temperature information to facilitate control of the sensor 1003.

Storage portion 1023 may be any suitable electronic storage medium. For example, storage portion 1023 may be non-volatile memory or other suitable computer readable memory. The power supply 1024 may be any suitable power supply, including a battery, plurality of batteries, transformer in communication with an external voltage source, or any other power supply disposed to provide power to the sensor control portion 1022, storage portion 1023, and the calibration portion 1025. The calibration portion 1025 may be a manual calibration means, including a switch, knob, button-system, or any other suitable calibration mechanism capable of providing selective control of the sensor 1003 and the thermocouple 1004.

The system 1000 further includes external interface 1001 in communication with the interface 512. For example, external interface 1001 may be a computer apparatus or processor, configured and disposed to communicate with the interface 512 over communication medium 1010. According to at least one example embodiment, the external interface 1001 is a dedicated interface disposed to monitor the probe 1003 and the thermo couple 1004 in a dedicated manner. Alternatively, the external interface may also be a programmable computing apparatus or processor disposed to monitor the probe 1003 and the thermocouple 1004 in a programmable manner (e.g., programmable temperature/oxygen control curves, etc).

Figure 11:
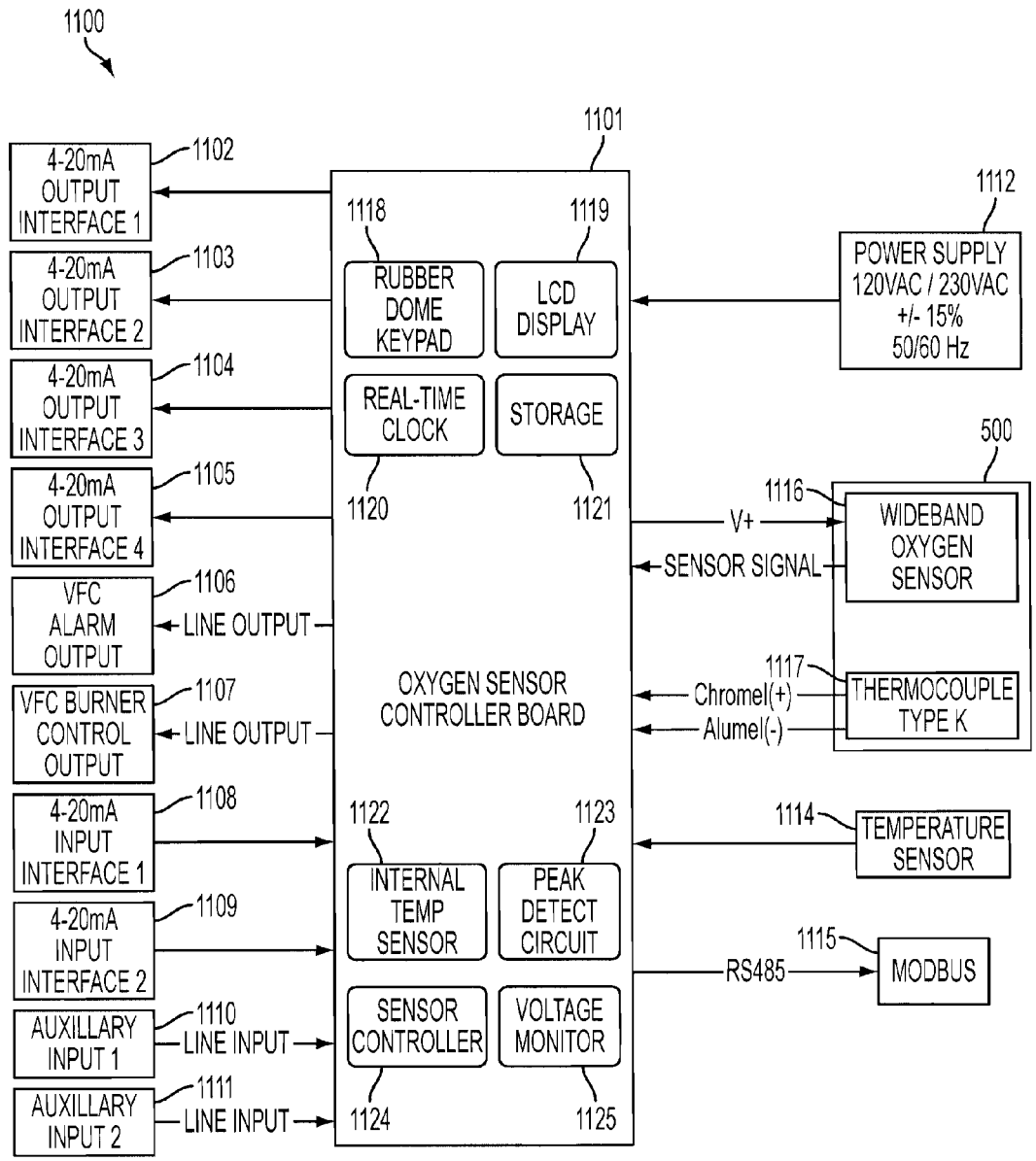
FIG. 11 depicts a control system of an oxygen measuring apparatus, according to an example embodiment.

FIG. 11 depicts an alternative control system of an oxygen measuring apparatus, according to an example embodiment. As illustrated, the system 1100 includes an electronic control interface 1101. The electronic control interface 1101 may include a plurality of control portions. For example, the interface 1101 may include input means 1118. Input means 1118 may be a plurality of pushbuttons, a keypad, a sequence of knobs, a combination of the same, or any other input means disposed to allow user control of an oxygen measuring apparatus. The interface 1101 may further include display means 1119. Display means 1119 may be a numerical display, alpha-numerical display, a liquid crystal display, a bank of indicator lights, or any combination of the same. The interface 1101 may further include clock 1120. Clock 1120 may be a real-time clock or any time-measuring apparatus configured to provide a clock signal for operation of the interface 1101 including log-times or other time information. The interface 1101 may further include storage 1121. Storage 1121 may be any suitable storage means, for example, as described above with reference to interface 512. The interface 1101 may further include an internal temperature sensor 1122 configured to monitor the temperature of the actual interface 1101. The interface 1101 may further include curve and/or peak detection circuit 1123 configured to monitor sensor output to determine when/if a peak in sensor output has occurred. The interface 1101 may further include sensor controller 1124. The sensor controller 1124 may be somewhat similar to sensor controller 1022 described above. Furthermore, the interface 1101 may include voltage monitor 1125.

Turning back to FIG. 11, the system 1100 may also include a power supply 1112 in communication with the interface 1101. The power supply 1112 may be any suitable power supply capable of providing power to the interface 1101.

The system 1100 may further include oxygen sensor 1116 and thermocouple 1117. The sensor 1116 and thermocouple 1117 may be somewhat similar to the sensor 1003 and the thermocouple 1004 described above.

The system 1100 may further include temperature sensor 1114 in communication with the interface 1101. For example, the temperature sensor 1114 may be arranged within a housing of an oxygen measuring apparatus.

The system 1100 may further include a communication interface 1115. The communication interface 1115 may be a serial interface, MODBUS interface, or any other suitable interface configured to establish communication between the interface 1101 and any desired external controller/computing apparatus.

Furthermore, the system 1100 may include a plurality of signal interfaces 1102-1111 configured to provide signals to/from the interface 1101 and a boiler system/external computing apparatus. For example, output signals 1102-1105 may provide information about flue stack temperature/oxygen content. Alarm outputs 1106-1107 may provide alarm signals associated with burner control. Additionally, inputs 1108-1111 may provide inputs to the interface 1101 for external modification/control of the interface 1101.

As describe above, a novel, low-cost oxygen measuring apparatus and associated control systems are provided. The oxygen measuring apparatus may include an oxygen measuring portion or cartridge which is easily replaceable and controlled. Thus, technical benefits include reduced costs associated with maintenance and replacement of oxygen sensors in boiler systems.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions, or equivalent arrangement not hereto described will be apparent to those of ordinary skill in the art without departing from the scope and spirit of the invention. Additionally, while various embodiment of the invention have been described, it is to be understood that aspects of the invention may include only some of the described embodiments. Accordingly, the invention is not to be seen as limited by the foregoing description, but is only limited by the scope of the appended claims.

The invention claimed is:

1. An oxygen measuring apparatus, comprising:
  an inlet pipe having a first end and a second end;
  an oxygen sensor arranged inside the inlet pipe between the first end of the inlet pipe and the second end of the inlet pipe, the oxygen sensor having a communication medium disposed thereon and extending through the second end of the inlet pipe;
  a filtering medium arranged inside the inlet pipe between the oxygen sensor and the first end of the inlet pipe;
  a housing arranged against the second end of the inlet pipe; and
  a sensor control interface arranged within the housing and in communication with the communication medium of the oxygen sensor.

2. The apparatus of claim 1, further comprising a thermal break between the oxygen sensor and the housing, wherein the communication medium of the oxygen sensor extends through the thermal break.

3. The apparatus of claim 2, further comprising a thermal gasket arranged between the thermal break and the housing.

4. The apparatus of claim 1, further comprising a thermocouple arranged on an exterior wall of the inlet pipe and extending through a wall of the housing arranged against the inlet pipe.

5. The apparatus of claim 4, wherein the sensor control interface is in communication with the thermocouple.

6. The apparatus of claim 1, further comprising an inner tube arranged inside the housing, wherein the communication medium of the oxygen sensor extends through the inner tube.

7. The apparatus of claim 6, further comprising a thermal break surrounding the inner tube and arranged against a wall of the housing arranged against the inlet pipe.

8. The apparatus of claim 7, further comprising a thermal gasket arranged between the thermal break and the wall of the housing.

9. The apparatus of claim 8, further comprising a thermocouple arranged on an exterior wall of the inlet pipe and extending through the wall of the housing.

10. The apparatus of claim 9, wherein the sensor control interface is in communication with the thermocouple.

11. An oxygen measuring apparatus, comprising:
  an inlet pipe having a first end and a second end;
  an oxygen sensing cartridge arranged inside the inlet pipe, the oxygen sensing cartridge having an outer wall in contact with an inner wall of the inlet pipe, a first end in contact with the second end of the inlet pipe, a communication medium disposed thereon, and a filtering medium arranged therein;
  a housing arranged between the second end of the inlet pipe and the first end of the oxygen sensing cartridge; and
  a sensor control interface arranged within the housing and in communication with the communication medium of the oxygen sensing cartridge.

12. The apparatus of claim 11, further comprising a thermal break between the oxygen sensing cartridge and the housing.

13. The apparatus of claim 12, further comprising a thermal gasket arranged between the thermal break and the housing.

14. The apparatus of claim 11, further comprising a thermocouple arranged on an exterior wall of the inlet pipe and extending through a wall of the housing.

15. The apparatus of claim 14, wherein the sensor control interface is in communication with the thermocouple.

16. The apparatus of claim 11, further comprising an inner tube arranged inside the housing and against the oxygen sensing cartridge.

17. A boiler control system, comprising:
  a combustion chamber;
  a flue stack in communication with the combustion chamber;
  a closed-loop boiler control portion in communication with the flue stack and the combustion chamber; and an oxygen measuring apparatus arranged on the flue stack;
   wherein the oxygen measuring apparatus includes:
      an inlet pipe having a first end and a second end, the inlet pipe extending through a wall of the flue stack;
      an oxygen sensing cartridge arranged inside the inlet pipe, the oxygen sensing cartridge having an outer wall in contact with an inner wall of the inlet pipe, a first end in contact with the second end of the inlet pipe and the wall of the flue stack, a communication medium disposed thereon, and a filtering medium arranged therein;
      a housing arranged around the second end of the inlet pipe, the first end of the oxygen sensing cartridge, and against the wall of the flue stack; and
      a sensor control interface arranged within the housing and in communication with the communication medium of the oxygen sensing cartridge.

18. The system of claim 17, wherein the closed-loop boiler control portion is in communication with the sensor control interface of the oxygen measuring apparatus.

19. The system of claim 18, further comprising an oxygen control servo in communication with the closed-loop boiler control portion and the combustion chamber and a fuel control servo in communication with the closed-loop boiler control portion and the combustion chamber, wherein the closed-loop boiler control portion is disposed to open or close the oxygen control servo and the fuel control servo in response to an output of the oxygen measuring apparatus.

20. The system of claim 17, wherein the closed-loop boiler control portion is disposed to increase or decrease a firing rate of the combustion chamber in response to an output of the oxygen measuring apparatus.

\* \* \* \* \*